United States Patent
Bakke

(10) Patent No.: US 6,608,968 B2
(45) Date of Patent: Aug. 19, 2003

(54) CONVECTION BLOOD WARMING SYSTEM WITH DISPOSABLE FLATTENED TUBE ENVELOPE INCORPORATING PAPERBOARD "NEEDLE" FOR INSERTING ENVELOPE BETWEEN HEATING PLATES AND EMPLOYING ACTIVE AND PASSIVE INSULATION OF OUTLET FLOW PATH TO PROVIDE NORMOTHERMIC FLUID AT ZERO TO 600 MILLILITERS PER MINUTE

(76) Inventor: Allan P Bakke, 3220 County View Ct. SW., Rochester, MN (US) 55902

( * ) Notice: Subject to any disclaimer, the term of this patent is extended or adjusted under 35 U.S.C. 154(b) by 0 days.

(21) Appl. No.: 10/292,749

(22) Filed: Nov. 12, 2002

(65) Prior Publication Data

US 2003/0099469 A1 May 29, 2003

Related U.S. Application Data

(60) Provisional application No. 60/335,862, filed on Nov. 23, 2001.

(51) Int. Cl.$^7$ .................................................. A61F 7/00
(52) U.S. Cl. ........................ 392/470; 392/471; 604/6.13
(58) Field of Search ................................ 392/470, 471; 604/6.13, 6.11, 6.14, 6.15, 903, 113, 153

(56) References Cited

U.S. PATENT DOCUMENTS

| | | | | | |
|---|---|---|---|---|---|
| 4,847,470 | A | * | 7/1989 | Bakke | 392/470 |
| 5,125,069 | A | * | 6/1992 | O'Boyle | 392/465 |
| 5,381,510 | A | * | 1/1995 | Ford et al. | 392/470 |
| 6,535,689 | B2 | * | 3/2003 | Augustine et al. | 392/470 |

* cited by examiner

Primary Examiner—Thor Campbell

(57) ABSTRACT

A thin, flat paperboard inserter or "needle" which is longer than the blood warmer heating plates is attached to the edge of the flattened tube envelope to enter the very narrow gap between the heating plates. The inserter is fed between the heating plates and advanced to emerge from the other end of the blood warmer where it is grasped and used to pull the envelope into operational position. A high air flow hydrophobic vent with check valve to prevent reverse flow is incorporated into the drip chamber to allow automatic priming and venting of air bubbles. A conductively heated and externally insulated drip chamber holder and a patient intravenous line that is passively insulated by a small annular air space extruded as part of the tube preserve heat in the warmed fluid, improving low flow rate performance. A reusable external heater may optionally be applied to the distal portion of the patient line to provide normothermic fluid to the patient down to essentially zero flow rate.

6 Claims, 6 Drawing Sheets

CONVECTION BLOOD WARMING SYSTEM WITH DISPOSABLE FLATTENED TUBE ENVELOPE INCORPORATING PAPERBOARD "NEEDLE" FOR INSERTING ENVELOPE BETWEEN HEATING PLATES AND EMPLOYING ACTIVE AND PASSIVE INSULATION OF OUTLET FLOW PATH TO PROVIDE NORMOTHERMIC FLUID AT ZERO TO 600 MILLILITERS PER MINUTE

CROSS REFERENCES TO RELATED APPLICATIONS

This application claims benefit of provisional aplication 60/335,862, filed Nov. 23, 2001.

The present invention relates to my two previous inventions U.S. Pat. Nos. 5,013,889 and 5,420,962. The present invention continues to use heating by vapor condensation employing flat plate heat pipes to warm blood through the walls of a thin plastic envelope heat exchanger. The improvements of this invention are applicable to other blood warmers not employing vapor condensation heating but which use resistively heated flat plate warming.

The present invention relates to delivering warm fluid to a patient at low flow rates, all the way down to essentially zero flow rate, providing fluid at 37 degrees C. leaving the patient line i.v. tubing 6 ft from the blood warmer outlet. This results in over-all warmer performance which delivers fluid warmed to at least 35C from zero to 600 ml/min when entering fluid is 10C.

The present invention also relates to my Provisional Patent Application No. 60/1335,862, Convective Blood Warming System with Disposable Flaftened Tube Envelope Incorporating Paperboard "Needle" for Inserting Envelope between Heating Plates and Employing Active and Passive Insulation of Outlet Flow Path to Provide Normothermic Fluid at Zero to 600 Milliliters per Minute, filed Nov. 23, 2001. The present invention essentially comprises the PPA of Nov. 23, 2001 which added the improvement of an externally applied, reusable, sensoriess control electric heater employed to actively warm the distal approximately 2 ft of the patient line. The combination of the heated drip chamber holder, the passively air insulated patient line and the active warming of the distal portion of the patient line synergistically results in over-all warmer performance which delivers fluid warmed to at least 35C from zero to 600 ml/min when entering fluid is 10C.

BACKGROUND—FIELD OF INVENTION

It has long been recognized that warming intravenous fluids to body temperature is beneficial and for rapid infusions of blood or other cold fluids such warming is necessary to prevent cardiac arrhythmias and possible cardiac arrest.

Fluid warmers have several challenges to meet. First, blood must not be overheated, or lysis of red cells occurs making the infusion toxic. Second, high flow rates are sometimes needed to replace blood volume in the event of rapid surgical blood loss. Most surgical cases, however, use only 1 to 2 liters of intravenous fluids over one or more hours, at low flow rates. Only a few blood warmers can meet the challenge of high flow rates (up to 500 ml/min), and most blood warmers can only effectively warm fluid at the low flow range down to about 25 ml/min.

The present invention provides both high and low flow rates (warms fluid from 10 to 35C from zero to 600 ml/min).

Further, it provides this superior performance using a single, low cost disposable.

BACKGROUND—DESCRIPTION OF PRIOR ART

My previous U.S. Pat. No. 5,420,962 related to a disposable system that incorporated a hydrophobic vent patch into the disposable envelope heat exchanger. It also provided for preservation of heat in the patient i.v. line by passing the i.v. line through a larger diameter (about 1 inch dia) flexible corrugated plastic tubing. Warm air was passed through the outer tube, bathing the i.v. line and reducing the heat loss to the ambient air.

U.S. Pat. No. 5,875,282 employs a flat envelope heat exchanger carried into position by a rigid plastic cassette and warms the heating plates directly with resistance heaters, but is less effective at high and low flow rates.

U.S. Pat. No. 5,063,994 utilizes a patient line with a central intravenous fluid lumen surrounded by a warm water carrying annular lumen which is divided in half. The warm water flows toward the patient in one half of the annular lumen, turns around 180 degrees and returns to the blood warmer, actively warming the intravenous fluid, but is only effective at low flow rates.

The present invention provides superior low flow rate performance by conductively heating the outlet drip chamber using heat from one of the heating plates, and also by passively insulating the i.v. line to the patient by employing an annular air space which surrounds the i.v. line with still air. The patient line tubing is a single extrusion, about 0.37 inch outside diameter polyvinyl chloride or other flexible plastic. This passive insulation of the patient line allows delivery of 35C fluid 4ft from the warmer outlet as low as 15 ml/min. A further improvement of the present invention is the addition of an optionally employed external temperature-controlled sensorless or sensor-controlled warmer to the distal portion of the patient intravenous line, actively warming and insulating approximately the distal 2 ft of patient line. For pediatric or other extremely low flow uses, this active warming of the distal line allows delivery of 37C fluid essentially down to zero flow rate.

SUMMARY

A new means of loading the flexible, floppy flattened envelope heat exchanger into the blood warmer apparatus is simple and economical, employing a paperboard inserter that passes easily through the very narrow slot between the two heating plates and then is grasped at the opposite end of the blood warmer and used to pull the envelope heat exchanger into place. This inserter eliminates the more complex stiff plastic cassette often used currently, and also allows closer spacing of the heating plates, resulting in more efficient heat transfer.

At low flow rates, blood cools by convection as it flows to the patient, negating the value of the blood warmer apparatus. The conductively warmed and externally insulated drip chamber holder of this invention in synergy and complementary action with a patient intravenous line that is insulated by an annular air space co-extruded with the central blood tube significantly reduce convective heat loss to the cooler ambient air. An optionally employed, temperature-controlled, reusable external heater may be applied to the distal portion of the patient line, allowing delivery of normothermic intravenous fluid to the patient at very low flow rates, down to essentially zero flow rate.

The improvements of this invention allow a single, low cost disposable system to provide warm blood or other fluid to the patient over the entire clinical range of useful flow rates, warming blood from 10 degrees C. to at least 35 C from zero ml/min to 600 ml/min by a compact, easy-to-use intravenous pole-mounted apparatus weighing less than 10 pounds.

OBJECTS AND ADVANTAGES

Accordingly, several objects and advantages of my invention are as follows. The present invention employs a thin semi-rigid paperboard inserter to load the flattened plastic envelope disposable heat exchanger between the fixedly mounted parallel heating plates which are closely spaced apart. Use of this inserter in place of a rigid plastic cassette to carry the disposable envelope allows the heating plates to be closer together, resulting in higher efficiency heat transfer.

A further object of the present invention is to allow delivery of warm fluid at low flow rates to the patient. Advantages working together in synergy to produce this result are the use of a heat conductive drip chamber holder sleeve closely attached to one of the heating plates to keep the drip chamber warm, and a flexible plastic patient line i.v. tubing with larger outside tubing extruded as part of the patient line. An annular air gap between the outer and inner tubes passively insulates the i.v. line from the cooler ambient air. Also, an optionally employed reusable external sensorless or sensor-controlled electric heater applied to the distal portion of the patient line actively warms fluid just before delivery to the patient at very low flow rates. These three improvements acting together in synergistic complementary action provide improvements in low flow performance not achieved before.

Another object of the present invention is to automatically vent high flow rates of air or bubbles from the flow path before infusion of fluid into the patient. It is well-known that infusion of air or gas into the veins of a patient may be lethal. In the present invention, a large (about 1 inch in diameter) hydrophobic vent is incorporated into the top of the drip chamber, capable of venting large volumes of air quickly. A commercially available check valve prevents reverse flow of air into the fluid flow path.

Still further objects and advantages will become apparent from a consideration of the ensuing description and accompanying drawings.

Figure 1:
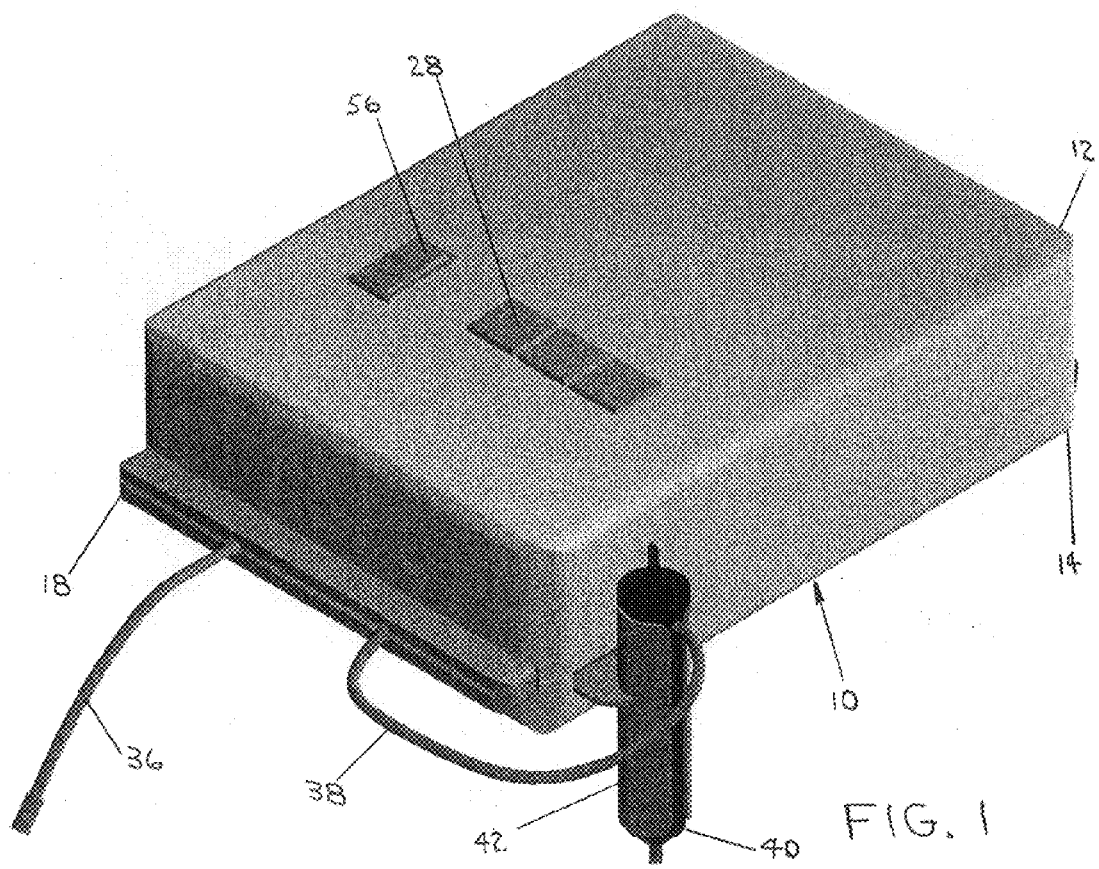
FIG. 1 is a perspective drawing of my invention

REFERENCE NUMERALS 10 blood warmer invention
12 front case
14 rear case
16 disposable heat exchanging blood warming envelope
18 inserter guide
22 front heat transfer plate
24 rear heat transfer plate
26 paperboard inserter
28 temperature controller
30 front etched foil heater
34 envelope retainer post
36 inlet tube
38 outlet tube
40 drip chamber
42 heated drip chamber holder
46 air insulated tubing
48 front stiffener
52 clamping screws
54 front epoxy spacer
56 power switch
58 transition tubing
60 tubing adapter
62 external heater
64 male luer lock adapter
66 electrical resistance heater
68 external heater wire
70 external heater connector

PREFERRED EMBODIMENT—DESCRIPTION

FIG. 1 shows the present blood warmer invention 10 with front case 12 and rear case 14 made from commercially available aluminum box enclosures about 0.06 inch thick. Disposable heat exchanging blood warming envelope 16 passes through inserter guide 18. Disposable heat exchanging blood warming envelope 16 lies between front heat transfer plate 22 and rear heat transfer plate 24 and is hidden from view in this drawing. Paperboard inserter 26 is attached to the rightmost end of disposable heat exchanging blood warming envelope 16 (FIG. 4), and is used to insert disposable heat exchanging blood warming envelope 16 between front heat transfer plate 22 and rear heat transfer plate 24, pulling it into operating position like a needle pulls thread.

Temperature controller 28 is seen protruding through front case 12 and is activated by power switch 56. Thermistor inputs from several locations on front heat transfer plate 22 and rear heat transfer plate 24 allow close temperature control of front heat transfer plate 22 and rear heat transfer plate 24 which are flat heat pipes heated by front etched foil heater 30 and a similarly mounted rear etched foil heater, neither of which can be seen in this figure. A power cord plugs into blood warmer invention 10 at the long side of front case 12 opposite drip chamber holder 42, and is not shown.

In operation cold blood or fluid enters the disposable heat exchanging blood warming envelope 16 through inlet tube 36, flows through disposable heat exchanging blood warming envelope 16 and exits through outlet tube 38 flowing through a flexible plastic tube to drip chamber 40 which is nested in heated drip chamber holder 42. Heated drip chamber holder 42 has a flat plate attached which is bonded with good thermal contact to the outside surface of rear heat transfer plate 24. Because heated drip chamber holder 42 is made of aluminum or other highly heat conductive metal and is covered with a thin layer of insulating material, it preserves warmth of fluid in drip chamber 40. A large (about 1 to 3 inch diameter) hydrophobic vent membrane is incorporated into the top of drip chamber 40 to automatically vent air or gas bubbles from the flow path. Fluid entering the drip chamber enters from the side, so that air may vent out the top opening, which will be protected by a commercially available check valve to prevent inflow of air. Fluid then exits at the lower end of drip chamber 40 and continues past a flow control roller clamp (not shown) which adjustably clamps transition tubing 58, and then flows through air insulated tubing 46 to the patient. Transition tubing 58 connects drip chamber 40 to air insulated tubing 46 through tubing adapter 60. External heater 62 may be optionally applied to the distal portion of air insulated tubing 46 to assist in maintaining fluid warmth at very low flows. External heater 62 maintains a controlled temperature of approximately 42C using a controller mounted inside blood warmer invention 10. External heater 62 is heated by electrical resistance heater 66, and is connected to its controller using external heater wire 68 and external heater connector 70. Air insulated tubing 46 is connected to the patient using male luer lock adapter 64, usually through a short extension having an injection site and a shut-off clamp.

Figure 2:
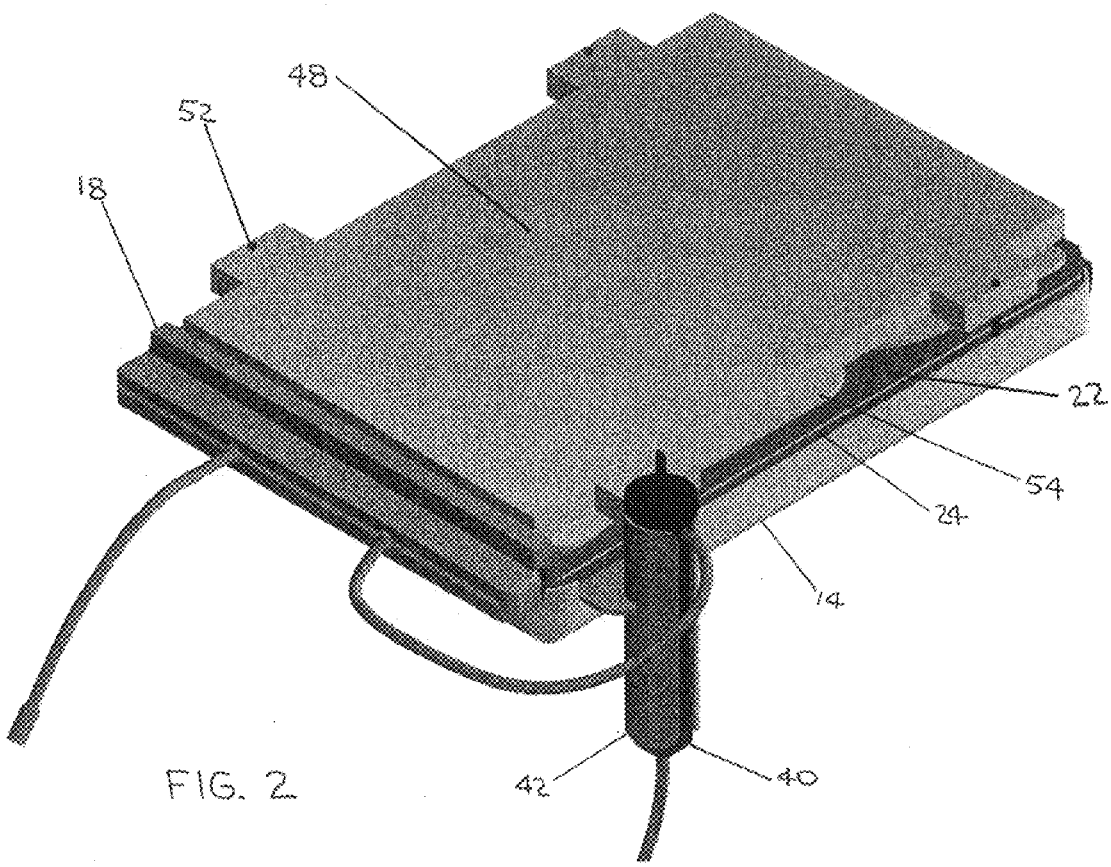
FIG. 2 is a perspective drawing of my invention with front cover removed

FIG. 2 shows blood warmer invention 10 with front case 12 removed so that front stiffener 48 is seen. A rear stiffener is similarly mounted behind rear heat transfer plate 24, and both stiffeners are made of light weight aluminum honeycomb or similar material about 0.5 inch thick. The stiffeners are needed to support the thin heating plates against internal pressure of the fluid being warmed of up to 300 mm Hg or about 6 psig. Front heat transfer plate 22 and rear heat transfer plate 24 are seen, as are clamping screws 52 which clamp front stiffener 48, front heat transfer plate 22, rear heat transfer plate 24, and rear stiffener 50 firmly together. Front heat transfer plate 22 and rear heat transfer plate 24 are spaced apart by metal or plastic shim spacers about 0.040 to 0.050 thick. Disposable heat exchanging blood warming envelope 16 is made of flexible polyethylene or other plastic with walls about 4 mils thick (0.004 inch). Thus the flow channel for fluid being warmed is about 0.032 to 0.042 inch deep.

Figure 3:
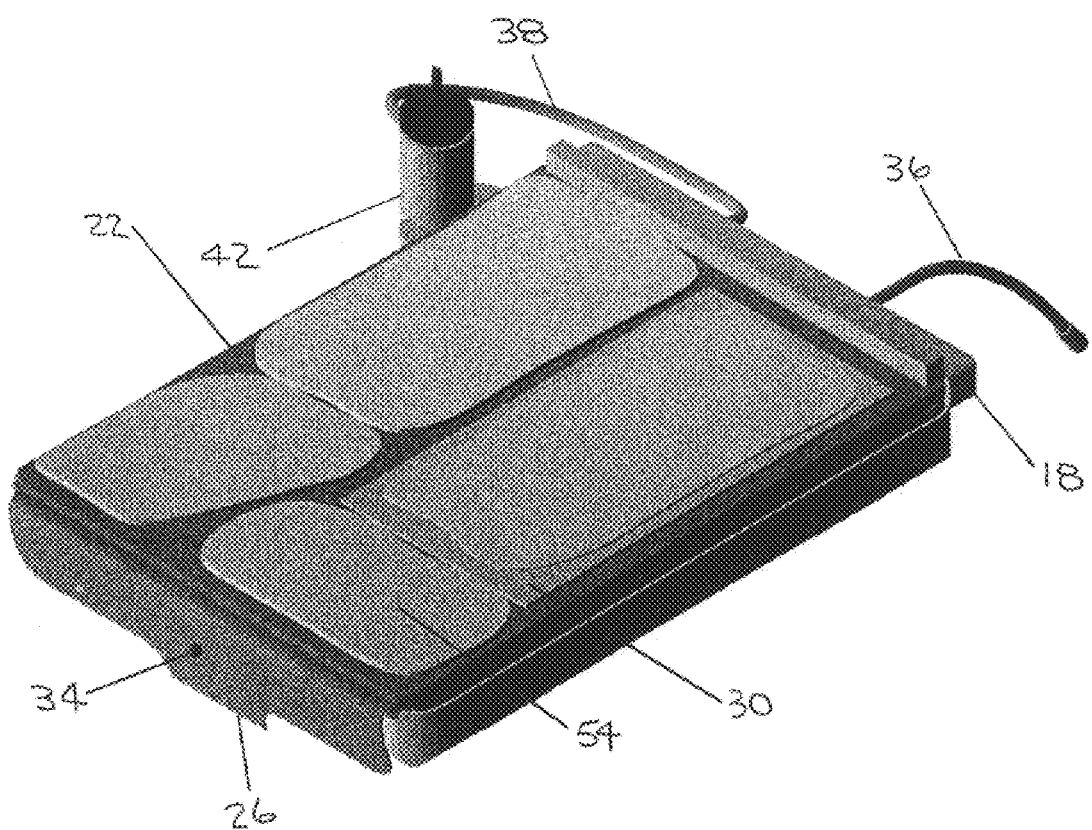
FIG. 3 is a perspective drawing of my invention with front cover and front stiffener removed

FIG. 3 is similar to FIG. 2, but front stiffener 48 has been removed to reveal front etched foil heater 30 bonded to the outer surface of front heat transfer plate 22. The uneven appearing front epoxy spacers 54 serve to fill gaps between front stiffener 48 and front heat transfer plate 22 so that front heat transfer plate 22 is uniformly supported. Epoxy spacers are employed similarly between rear stiffener and rear heat transfer plate 24.

Figure 4:
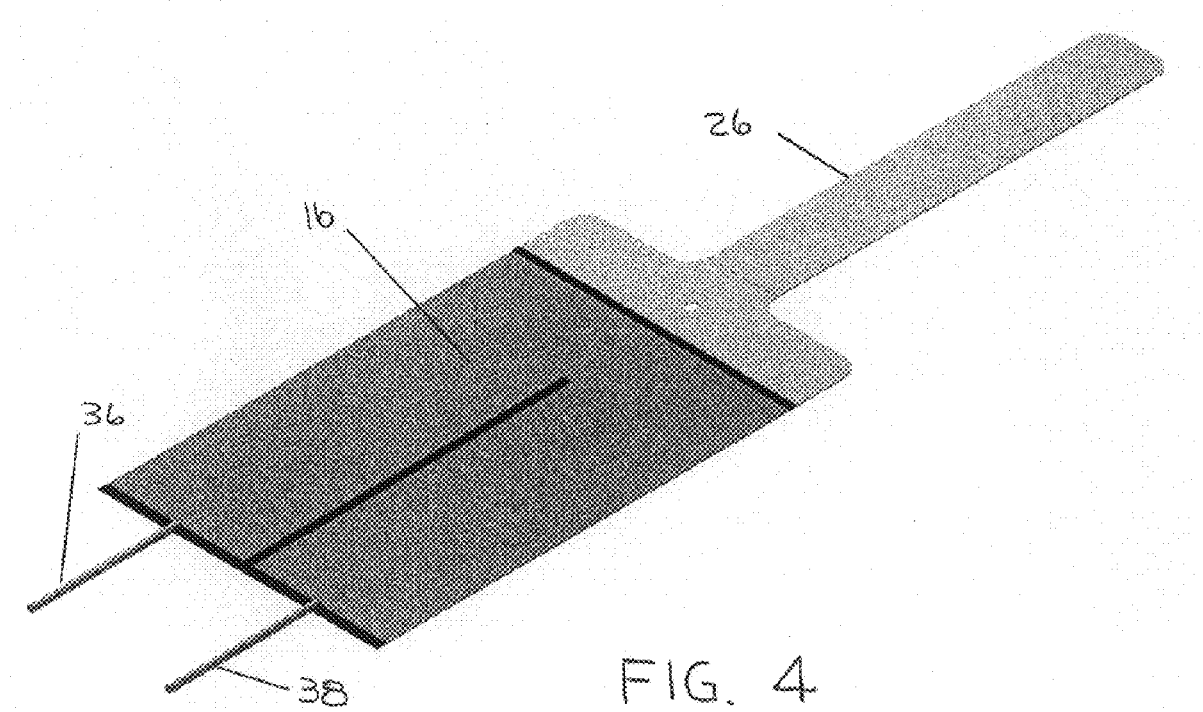
FIG. 4 is a perspective drawing of the disposable envelope with inserter

FIG. 4 shows disposable heat exchanging blood warming envelope 16 outside the blood warmer invention 10. The long tail of the paperboard inserter 26 is marked with a dashed line where it is torn off after insertion of disposable heat exchanging blood warming envelope 16. Also shown is a small hole, about 0.25 to 0.38 inch diameter, which engages envelope retaining post 34 on the rear case 14 to hold disposable heat exchanging blood warming envelope 16 in place during operation. Flow in disposable heat exchanging blood warming envelope 16 enters at inlet tube 36, proceeds as a thin ribbon of fluid to the right end where it is constrained to turn 180 degrees and to exit through outlet tube 38.

After use, disposable heat exchanging blood warming envelope 16 is easily removed from blood warmer invention 10 by clamping off inlet tubing between disposable heat exchanging blood warming envelope 16 and fluid source to allow fluid to drain from disposable heat exchanging blood warming envelope 16. After disposable heat exchanging blood warming envelope 16 has been removed from blood warmer invention 10, entire disposable system is removed from the i.v. and the i.v. set is re-connected to the patient.

Figure 5:
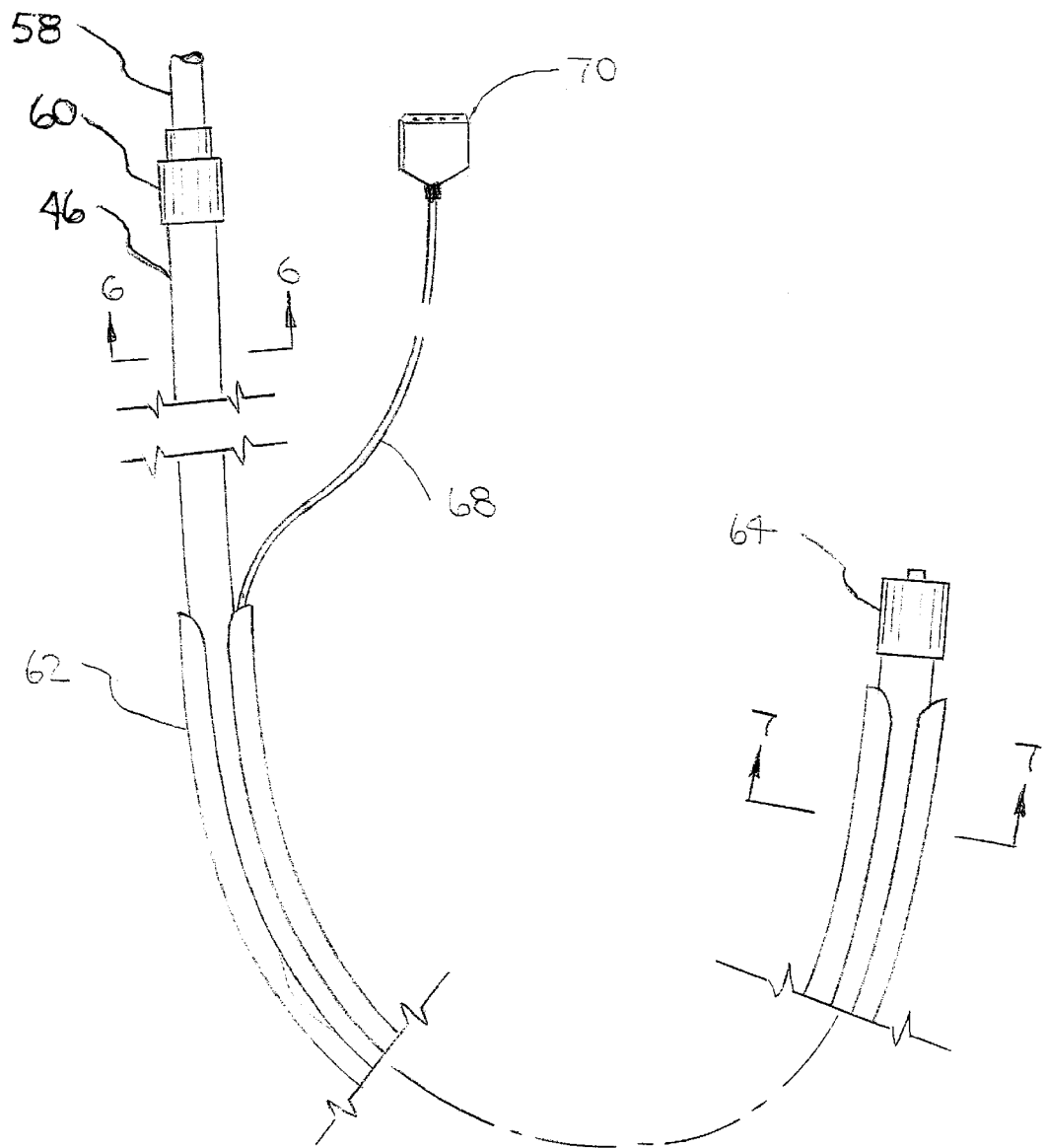
FIG. 5 is a drawing of the air insulated patient line with external heater

FIG. 5 shows the air insulated tubing 46 which conveys the warmed blood or fluid from the drip chamber 40 to the patient. Also shown is the external heater 62 which is temperature-controlled using either sensorless or sensor-controlled electrical resistance heater 66. External heater 62 removably surrounds the distal portion of air insulated tubing 46 (the patient line), helping to maintain its temperature at about 42C to prevent convective cooling by ambient cooler air.

Figure 6:
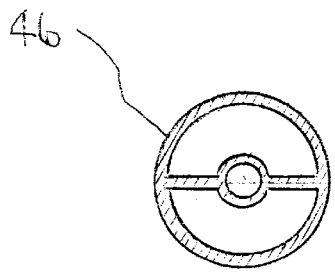
FIG. 6 is a cross-sectional view of air insulated patient line on line 6—6 of FIG. 5 and in the direction of the arrows
Figure 7:
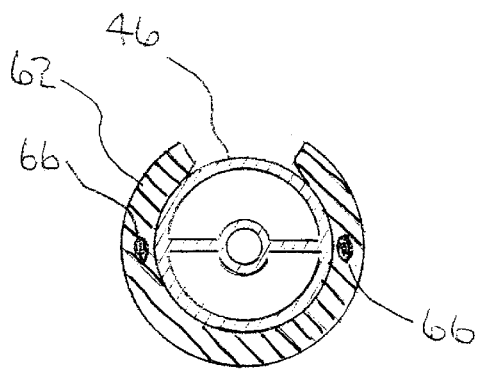
FIG. 7 is cross-sectional view of air insulated patient line and external heater on line 7—7 of FIG. 5 and in the direction of the arrows
Figure 7A:
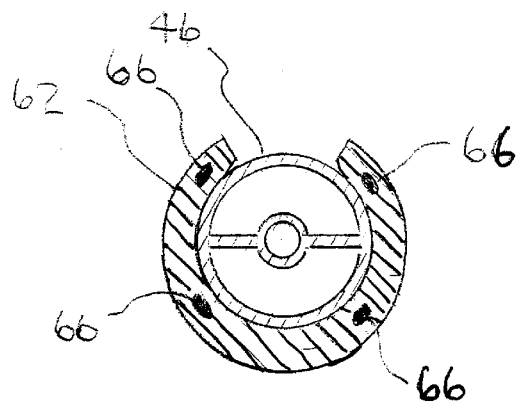
FIG. 7a is another embodiment of the external heater shown in FIG. 7

FIGS. 6, 7, and 7a show cross-sectional views of the air insulated tubing 46 patient line and the reusable external heater 62 which may optionally be applied to the distal portion of the air insulated tubing 46 patient line to allow delivery of normothermic fluid at very low flow rates.

PREFERRED EMBODIMENT—OPERATION

In operation blood warmer invention 10 is powered by a power cord being plugged into a surgical a.c. power supply, and is turned on at power switch 56. Disposable heat exchanger envelope 16 is positioned by first inserting paperboard inserter 26 through slot in inserter guide 18 and pushing it through blood warmer invention 10 until it emerges at other end between front heating plate 22 and rear heating plate 24. Paperboard inserter 26 is then grasped and used to pull disposable heat exchanger envelope 16 into place. Tail of paperboard inserter 26 is removed by tearing at perforation, and the hole in remaining part of paperboard inserter 26 is engaged with retainer post 34 on rear case, thus holding disposable envelope 16 in operational position.

Drip chamber 40 is then inserted into heated drip chamber holder 42. Intravenous supply source is attached to inlet tube 36 and the disposable system is primed by turning on the intravenous source until the drip chamber fills and bubble-free fluid drips from end of air insulated tubing 46. The end of air insulated tubing 46 is then attached to the patient through a short i.v. extension. External heater 62 may be applied to distal end of air insulated tubing 46 and external heater wire 68 plugged into its controller using external heater connector 70. Flow rate is controlled by a roller clamp on transition tubing 58. Warm intravenous fluid is then administered as needed to the patient at rates of zero to 600 ml/min until fluid warming is no longer needed.

The disposable heat exchanger envelope 16 may be easily removed from blood warmer invention 10 by leaving outlet tube 38 open and clamping off inlet tube 36, so that fluid drains out of disposable heat exchanger envelope 16. Disposable heat exchanger envelope 16 may then be easily removed after paperboard inserter 26 is released from retainer post 34 on rear case 14.

Disposable system is removed from flow circuit by first clamping off extension at patient and at intravenous source. Also to be clamped off are inlet tube 36 and outlet tube 38. The disposable system is then removed from the patient and from the intravenous source, and the intravenous source is re-connected to the patient's short i.v. extension.

The patient may then be transported from the operating room.

CONCLUSIONS, RAMIFICATIONS, AND SCOPE

Accordingly, it can be seen that the present invention provides numerous improvements to blood warming practice, resulting from novel and unobvious changes in the case of the paperboard inserter 26 and heated drip chamber holder 42, and by improvements in low flow performance resulting from complementary and synergistic effects of the heated drip chamber holder 42, air insulated tubing 46, and external heater 62 working together to preserve heat and insulate against the convective cooling effects of ambient air.

Although the description above contains many specificities, these should not be construed as limiting the scope of the invention but as merely providing illustrations of some of the presently preferred embodiments of this invention. Various other embodiments and ramifications are possible within its scope. For example, although this disposable system invention is applied to my previous vapor condensation blood warmer (U.S. Pat. No. 5,013,889), it would provide significant improvement to several other currently marketed flat plate dry heat blood warmers, and the combination of the heated drip chamber holder 42, air insulated tubing 46, and external heater 62 would enhance the low flow performance of several other fluid warmers not of the flat plate dry heat variety.

Thus the scope of the invention should be determined by the appended claims and their legal equivalents, rather than by the examples given.

What is claimed is:

1. A system for warming blood or other liquids to body temperature for infusion into a patient comprising:
    A.) a blood warmer apparatus having a pair of fixedly closely spaced apart heat transfer plates adapted to receive a flat heat exchanging blood warming envelope between said fixedly closely spaced apart heat transfer plates, wherein the gap between said fixedly closely spaced apart heat transfer plates is exposed at two opposite ends forming a wide slot,
    B.) an inserter for positioning said flat heat exchanging blood warming envelope between said fixedly closely spaced apart heat transfer plates including,
        1.) a sheet of semi-rigid material slightly thinner and narrower and longer than said wide slot formed by the gap between said fixedly closely spaced apart heat transfer plates,
        2.) means for attaching said sheet of semi-rigid material to said flat heat exchanging envelope along its insertion edge,
        3.) means such as perforations for tearing off or otherwise removing all but about 2 inches of said sheet of semi-rigid material after it has been used to insert and position said blood warming envelope,
        4.) means such as a hole about 0.25 to 0.38 inch in diameter in the remaining approximately 2 inches of said semi-rigid material for attaching it to a post or other attaching means fixedly mounted appropriately on rear case of said blood warmer apparatus after said semi-rigid material has been used to insert and position said blood warming envelope,
    whereby a person can easily insert and correctly position said flat heat exchanging blood warming envelope in said blood warming apparatus.

2. A system for warming blood or other liquids to body temperature for infusion into a patient comprising:
    A.) a blood warmer apparatus having a pair of fixedly closely spaced a heat transfer plates adapted to receive a flat heat exchanging blood warming envelope between said fixedly closely spaced apart heat transfer plates, wherein the gap between said fixedly closely spaced apart heat transfer plates is exposed at two opposite ends forming a wide slot,
    B.) said flat heat exchanging blood warming envelope having a blood inlet tube adapted to be connected to a source of blood to be warmed and a blood outlet tube adapted to be connected to a blood drip chamber adapted to be connected to a flow line to the patient, said drip chamber adapted to be supported inside a warmed drip chamber holder,
    C.) said flow line to the patient being a flexible tube made of polyvinyl chloride or other resinous plastic material,
    D.) said drip chamber holder being made of aluminum or other highly heat conductive material about 0.06 inch thick and having a flat sheet of said material about 2 to 4 inches wide and 3 to 6 inches long welded or otherwise heat conductively attached to said holder, said flat sheet being heat conductively attached by epoxy adhesive or other attaching means to the outside of one of said heat transfer plates,
    E.) said drip chamber holder being coated on its outer surfaces with a layer of heat insulating material about 0.06 inch thick,
    whereby blood passing slowly through said drip chamber is maintained near the temperature of said heat transfer plates and heat from blood being warmed is not lost to the ambient air by convection.

3. A system according to claim 2 wherein said drip chamber and said warmed drip chamber holder are approximately cylindrical in shape with diameters about 1 to 3 inches and heights about 2 to 5 inches.

4. A system according to claim 2 wherein the distal portion of said flexible tube flow line is removably inserted into an external heater,
    A.) said external heater being comprised of an elongated flexible plastic or silicone rubber tube having a cross-section in the form of a "C", with a wall thickness of approximately 0.12 inch, closely fitting around said flexible tube flow line,
    B.) said external heater being heated electrically by an electrical resistance heater embedded in the wall or in an extruded elongated cavity in the wall of said external heater, extending for the full length of said heater,
    C.) said electrical resistance heater being maintained at a controlled temperature of about 42C by a controller mounted inside said blood warmer apparatus,
    whereby in synergistic and complementary effect with said drip chamber holder heat is preserved in the blood as it flows slowly to the patient by reducing heat loss by convection to the ambient cooler air.

5. A system according to claim 2 wherein said flexible tube flow line has a central blood-carrying tube about 0.12 inch inside diameter and a wall thickness of about 0.04 inch, and is supported inside a larger tube which is co-extruded with said central tube and has an outside diameter of about 0.37 inch and a wall thickness of about 0.04 inch, said central and outer tubes being interconnected by co-extruded webs about 0.04 inch thick which appear in cross section as a planar diametrical web across the entire cross section with the exception of said central tube's lumen, wherein an annular space between said central and outer tubes is filled with heat insulative still air,
    whereby in synergistic and complementary effect with said drip chamber holder heat is preserved in the blood as it flows slowly to the patient by reducing heat loss by convection to the ambient cooler air.

6. A system according to claim 5 wherein the distal portion of said flexible tube flow line is removably inserted into an external heater, A.) said external heater being comprised of an elongated flexible plastic or silicone rubber tube having a cross-section in the form of a "C", with a wall thickness of approximately 0.12 inch, closely fitting around said flexible tube flow line, B.) said external heater being heated electrically by an electrical resistance heater embedded in the wall or in an extruded elongated cavity in the wall of said external heater, extending for the full length of said heater, C.) said electrical resistance heater being maintained at a controlled temperature of about 42C by a controller mounted inside said blood warmer apparatus, whereby in synergistic and complementary effect with said drip chamber holder and said flexible tube flow line heat is preserved in the blood as it flows slowly to the patient by reducing heat loss by convection to the ambient cooler air.

* * * * *